(12) United States Patent
Sage

(10) Patent No.: US 7,216,081 B1
(45) Date of Patent: May 8, 2007

(54) INTERACTIVE PROCESS AND SYSTEM FOR SCREENING CYTOLOGICAL SPECIMENS

(75) Inventor: Robert M. Sage, Holliston, MA (US)

(73) Assignee: Psyche Systems Corporation, Milford, MA (US)

( * ) Notice: Subject to any disclaimer, the term of this patent is extended or adjusted under 35 U.S.C. 154(b) by 896 days.

(21) Appl. No.: 10/400,228

(22) Filed: Mar. 27, 2003

(51) Int. Cl.
*G10L 13/00* (2006.01)
*G02B 2/26* (2006.01)
*G01J 1/20* (2006.01)
*G06K 9/00* (2006.01)

(52) U.S. Cl. .............. 704/258; 704/270; 704/260; 359/393; 359/396; 250/201.3; 250/201.8; 382/128

(58) Field of Classification Search ........ 704/270–275, 704/258, 260; 250/201.3, 201.8; 359/393, 359/396; 382/128
See application file for complete search history.

(56) References Cited

U.S. PATENT DOCUMENTS 5,677,966 A * 10/1997 Doerrer et al. ............. 382/128
5,790,308 A * 8/1998 Kamentsky ................. 359/393

* cited by examiner

*Primary Examiner*—Vijay B. Chawan
(74) *Attorney, Agent, or Firm*—Altman & Martin

(57) ABSTRACT

Concentration by cytology personnel, i.e. users, is induced during scanning and marking of cytology slides, by electronic recognition of parsed voice inputs that are spoken by the users, electronic generation of selected voice output alerts that are heard by the users, and electronic processing of the voice inputs and voice outputs, for semi-automatic development of a cytology report.

15 Claims, 8 Drawing Sheets

| Step 1 - Provide Case Number<br><br>User speaks entire number or only last 6 digits | System responds by speaking patient's name if match is found. If match is not found, system responds by speaking "No Match Found" |
|---|---|
| Step 2 - Verify Case<br><br>User speaks request for one of: Social Security No., Medical Record, Birth Date, or Case Number | System responds with requested information. If input was "Continue", system speaks "Ready For Adequacy" in response |
| Step 3 – Provide The Adequacy<br><br>The adequacy will be either Satisfactory, Unsatisfactory, or Satisfactory Limited (non-Bethesda protocol only) | In response, system speaks either "Ready For Diagnosis" or "Ready For Specimen Comment" |
| Step 4 – Provide Specimen Comment<br><br>Comment is selected from Specimen Comment Library | System responds by speaking specimen comment that has been entered.<br>If Adequacy is Satisfactory, system speaks "Ready for Diagnosis". If Adequacy is Unsatisfactory, system speaks "Ready For Sign Out" |
| Step 5 – Provide Diagnosis<br><br>Diagnosis includes list of diagnosis phrases assembled from Library Of Diagnosis Phrases | System speaks the general Diagnosis category and "Ready to Sign Out" |
| Step 6 – Sign Case Out<br><br>User speaks "Sign Case Out" or if applicable, "Sign Case Out With Review" or "Sign Case Out With Re-screen". | System speaks "Case Signed Out" and repeats diagnosis.<br>When system speaks "Ready For Case Number", system is ready for next case. |

Fig. 3

| Command | System Response |
|---|---|
| "Clear the Case" | System clears current case in memory. No database updates are performed. User is placed at first step in pap process (providing a case number). System responds by speaking "Ready For Case Number" |
| "Back" | System returns to previous step in pap process thus allowing user to edit erroneous selections. "Back", while in Add Mode, functions the same as "Done Adding". |
| "Where Am I" | System responds by speaking the current process to User. For example, if User at beginning of pap process speaks "Where Am I", system speaks "You Are Getting The Case". |
| "Repeat" | System repeats its last spoken output. |
| "Sleep" | System speaks "Sleeping" and effectively stops listening to all commands. System only responds to "Wake Up". |
| "Wake Up" | System speaks "I'm Awake" and allows user to continue where he/she left off. |
| "Log Out" | System speaks "Are You Sure You Want to Log Out". User must respond "YES" or "NO". |

Fig. 4

| User Remove All Command | System Response |
|---|---|
| Step 1 – Instruct system to remove all case information by speaking one of the following commands:<br>"Remove all supplemental report"<br>"Remove all notes"<br>"Remove all specimen information"<br>"Remove all comments"<br>"Remove all scratch pad" | The system determines if the request is applicable at the time that the command is made.<br><br>If the command is applicable, the system responds by indicating that the command has been completed and proceeds to the next step in the pap process. |

Fig. 5

| User Voice Input | System Voice Output |
|---|---|
| Step 1 – Enter Add Mode by speaking one of following commands:<br>"Add To Supplemental Report"<br>"Add To Notes"<br>"Add To Case Clinical Information"<br>"Add To Specimen Clinical Information"<br>"Add To Comments"<br>"Add Additional Specimen Comment"<br>"Add Additional Diagnosis" | System determines if the request is applicable at the time the command is made.<br><br>If the command is applicable, the system responds that it is ready to perform command. |
| Step 2 – Speak the phrase to be added. | System determines if phrase proposed to be added can be added.<br>If YES, system speaks "(phrase) Added" |
| Step 3 – Speak phrase "Done Adding" | System speaks<br>"Ready For Adequacy"<br>"Ready for Specimen Comment"<br>"Ready for Diagnosis"<br>"Ready for SignOut" |

Fig. 6

| User Spoken Inputs | System Spoken Outputs |
|---|---|
| Step 1 – User requests case information by speaking one of the following commands:<br>"Read supplemental report"<br>"Read notes"<br>"Read clinical information"<br>"Read specimen clinical information"<br>"Read comments"<br>"Read scratch pad"<br>"Read adequacy"<br>"Read specimen comment"<br>"Read diagnosis" | The system determines if the request is applicable at the time the command is made.<br><br>An example of a non-applicable command would be a user request to Read Notes when a case has not been selected and verified.<br><br>If a command is applicable, the system speaks an output that the request has been completed and proceeds to the next step in the pap process. |

Fig. 7

| User spoken input | System spoken output |
|---|---|
| Step 1 - User requests removal of case information by speaking on of following commands:<br>"Remove From Supplemental Report"<br>"Remove Notes"<br>"Remove Case Clinical Information"<br>"Remove Clinical Information"<br>"Remove Comments" | System determines if the request is applicable at the time that the command is made.<br><br>An example of a non-applicable command is if the user commands "Remove Notes" before a case has been selected and verified. System will speak that it cannot complete command and will speak an explanation of why it failed.<br><br>If the command is applicable, the system responds by speaking that it is ready to perform the command. |
| Step 2 – Provide phrase to remove. User speaks code or voice shortcut associated with item to be removed. | System determines if the phrase to be removed can be removed.<br><br>An example of a phrase that cannot be removed is a phrase that doesn't exist. The system speaks that cannot complete command and give an explanation of why.<br><br>If phrase can be removed, system will respond by speaking that the phrase has been removed and proceeds to next step in the pap process. |

Fig. 8

INTERACTIVE PROCESS AND SYSTEM FOR SCREENING CYTOLOGICAL SPECIMENS

RELATED APLICATIONS

Not Applicable

GOVERNMENT FUNDING

Not Applicable

BACKGROUND OF THE INVENTION

1. Field of the Invention

The present invention relates to cytology, the study of individual cells, and, more particularly, to screening collections of cells that have been taken from a medical patient for the purpose of medical diagnosis.

2. The Prior Art

Ordinarily, such a collection of cells, after being acquired by biopsy or aspiration, are spread on a glass slide, stained and preserved, and examined under a microscope by a cytologist, i.e. a cytotechnologist or a cytopathologist. One such procedure is called a pap smear, which is a screening test for uterine cancer. This procedure usually involves wiping the cervix of a patient to collect cells, smearing the cells onto a glass slide, and sending the resulting specimen to a laboratory. At the laboratory, a cytologist stains the specimen and examines the cells under a microscope for evidence of morbidity. The microscopic examination consists of moving the slide under the microscope in a series or raster of sequential scans. During scanning and while under the microscope, atypical cells are marked with ink dots or other symbols for later identification. This scanning procedure must be performed with unremitting attention, lest the cytologist miss cells with significant abnormalities. Because distances between cells and gradients between scans are microscopic, any interruption in or distraction from the screening process may result in omissions during a scan or in confusion between scans.

SUMMARY OF THE INVENTION

The primary object of the present invention is to provide processes and systems for minimizing the effect of interruptions in and distractions from the continuous visual attention needed when screening cytology slides. The processes and systems of the present invention tend to induce the user (the cytologist) to maintain eye contact with the cytology slide during scanning and marking by the use of interacting voice inputs from the user and voice outputs from the system. Preferably the voice inputs and outputs are in the form of parsed phrases that can be remembered easily by the user and processed easily by the system. Communication between the system and the user is in the form of voice inputs from the user and voice outputs from the system, which (1) enable the user to speak input comments for conversion to text in an electronic scratch pad regarding visual observations being made during scanning, (2) enable the user to call up the input comments as voice outputs, (3) enable the user to call up comments and diagnoses in the form of voice outputs from electronic comment and diagnosis vocabularies, (4) enable the user to hear the voice outputs at any time, and (5) enable the user to assemble a selection of the voice inputs and outputs in the same text format for the development of a cytology report.

BRIEF DESCRIPTION OF THE DRAWINGS

For a fuller understanding of the nature and objects of the present invention, reference is made to the following specification, which is to be taken in connection with the accompanying drawings, wherein:

FIG. 3 is a table illustrating steps of the process of the present invention;

FIG. 4 is a table illustrating key commands of the present invention;

FIG. 5 is a table showing a further command of the present invention;

FIG. 6 is a table showing a further command of the present invention;

FIG. 7 is a table showing a further command of the present invention;

FIG. 8 is a table showing further commands of the present invention;

DETAILED DESCRIPTION OF THE PREFERRED EMBODIMENT

Figure 1:
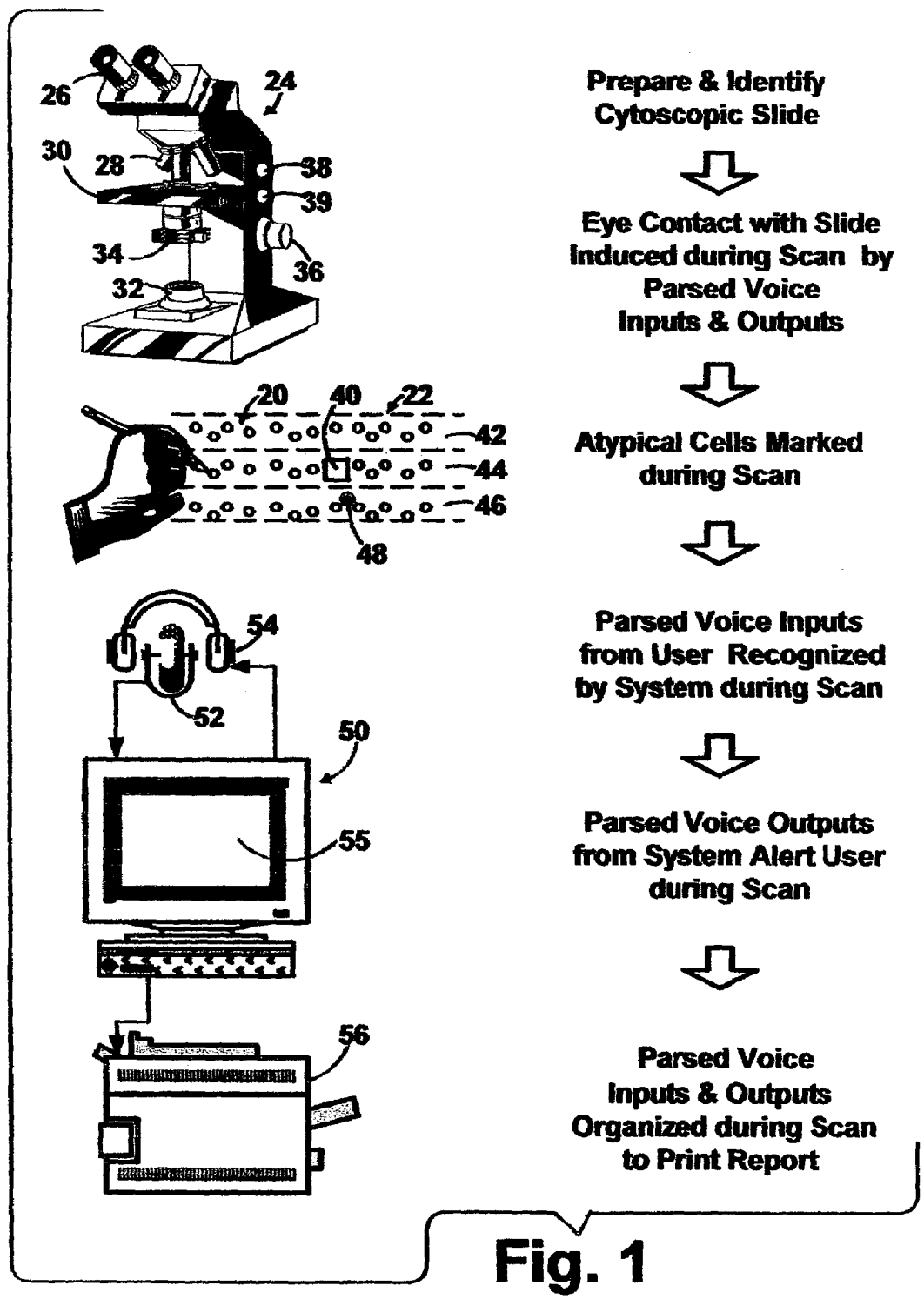
FIG. 1 shows the interaction between the physical and the electronic components of the present invention.

Interaction of the Physical and Electronic Components—FIG. 1

FIG. 1 illustrates a process and system embodying the present invention for screening a collection of cells 20, which have been acquired by biopsy or aspiration and have been spread on a glass slide, a magnified fragment of which is shown at 22. As shown, the cells have been stained and preserved for examination by a cytologist under a microscope 24. The microscope comprises a binocular 26, several objectives 28, a specimen stage 30, an upwardly directed lamp 32, and an optical condenser 34. Vertical focus is controlled by a knob 36. X,Y positioning on stage 30 is controlled by a pair of knobs 38, 39.

The microscopic examination consists of moving slide 22 on stage 30 under a microscope objective 28 past a viewing field 40, in a series or raster of sequential scans 42, 44, 46, etc., which are suggested by dashed lines. During scanning and while under the microscope, atypical cells are marked with an ink dot configuration 48 or other symbol for later identification.

The present invention maintains the attention of the cytologist by a dialog conducted between the cytologist and a computer system 50. During voice input, the cytologist speaks to the system. During voice output, the system speaks to the cytologist. The verbal components of this dialog are designed to induce the cytologist to maintain continuous eye contact with the slide being screened. The voice input is transmitted to the system via a microphone 52 and converted to text format by a voice recognition unit. The voice output is generated by a voice synthesizing unit and transmitted to the cytologist via earphones 54. The voice recognition engine and the voice synthesizer engine are of the types sold commercially by Microsoft Corporation under the trade designation MICROSOFT SPEECH API 5, which is included in a software kit that is sold by Microsoft Corporation under the trade designation MICROSOFT SPEECH SDK.

The processes and systems of the present invention tend to induce concentration by cytology personnel, during scanning and marking of the slides, by (1) electronic recognition of parsed voice inputs that are spoken by the cytologist, (2) electronic generation of parsed voice outputs that are heard by the cytologist, and (3) interactive electronic processing of the text upon which the voice inputs and voice outputs are based for semi-automatic development of a cytology report as at 56.

Figure 2:
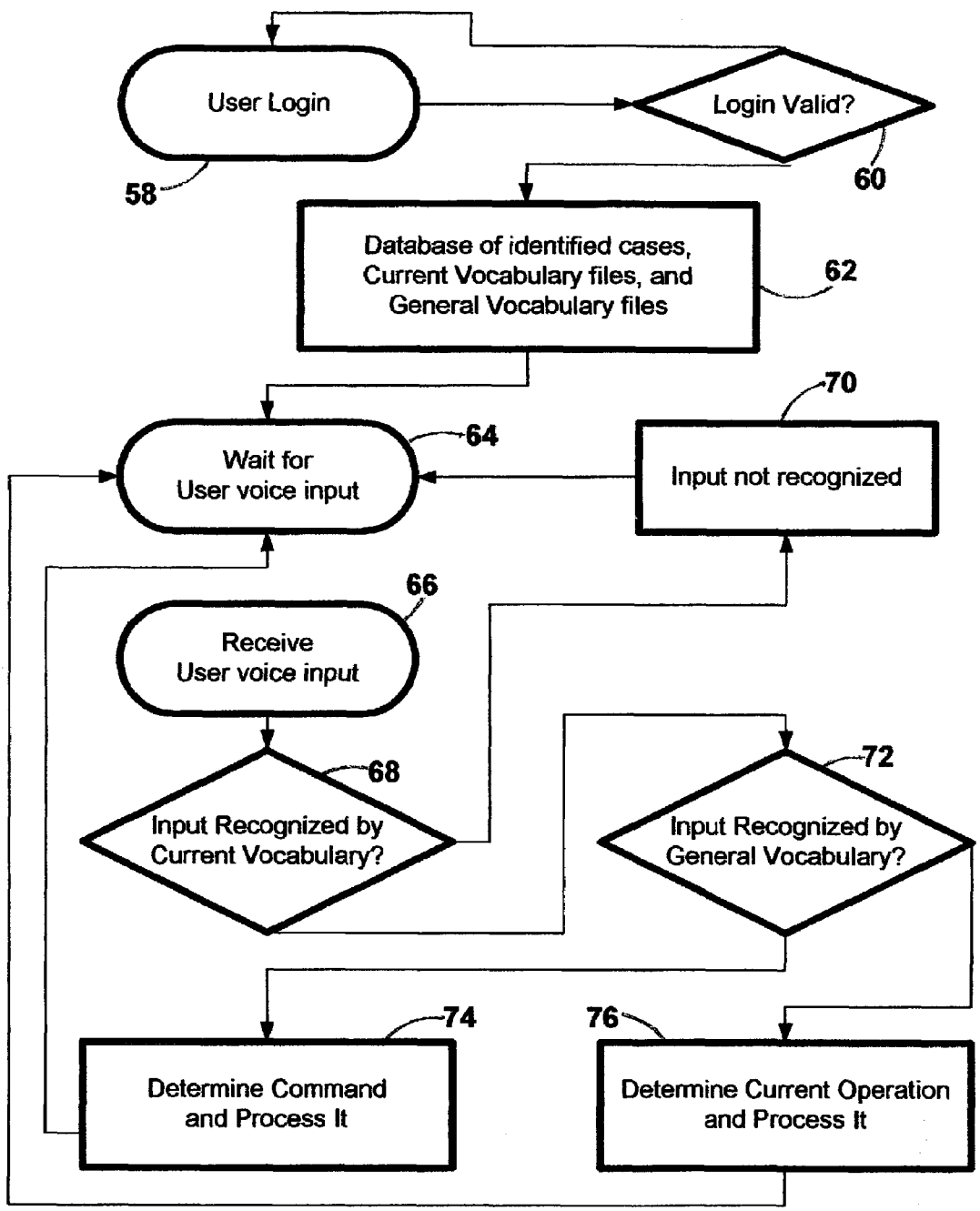
FIG. 2 is a general flow diagram of the process and system of the present invention.

General Principles—Flow Diagram of FIG. 2

The flow diagram of FIG. 2 illustrates the computer system broadly. When a cytologist logs in at a control 58 and if the Login is found valid by a decision procedure 60, a pap case requiring screening is retrieved from a database 62 and a control 64 is set to Wait. The cytologist proceeds as in FIG. 1 with scanning the slide that has been identified.

When, during the scanning procedure, the cytologist speaks a voice input in the form of a command or phrase that activates a control 66, focus is transferred to a decision procedure 68, which determines whether the voice input is recognized. If the output of decision procedure 68 is NO, the cytologist is notified, via speaker 54 and monitor 55 under the control of an output procedure 70, that the voice input is not recognized, and focus is returned to control 64. If the output of decision procedure 68 is YES, focus is transferred to a decision procedure 72, which determines whether the voice input from decision procedure 68 is one of the vocabulary phrases that are common to all of the vocabulary files in database 62. If the output of decision procedure 72 is YES, focus is transferred to vocabulary procedure 74. If the output of decision procedure 72 is NO, focus is transferred to current operation procedure 76.

Vocabulary procedure 74 retrieves vocabulary phrases and voice shortcuts that describe pap case outcomes for creation and presentation of vocabulary files. Current operation procedure 76 retrieves current operation commands that are appropriate for the selected vocabulary files. The procedures preferably are in XML format.

As will be described in more detail below in reference to FIG. 9, vocabulary processor 74 selects the appropriate command and executes it. As will be described in more detail below in reference to FIG. 10, current operations procedure 76 selects the current operation and executes it.

The Tables of FIGS. 3 to 8

FIGS. 3, 4, 5, 6, 7 and 8 explain the available commands and operations that are applied in the aforementioned procedures.

FIG. 3 shows the six primary processing steps of the illustrated embodiment of the present invention. The illustrated program responds at any time during the pap process to the commands that control these processing steps.

FIG. 4 shows the seven primary commands of the present invention. These commands are available to a user at any time during the pap process.

FIG. 5 shows the "Remove All" command. This provides the capability of removing all comments, notes, supplemental reports, case clinical information, and specimen clinical information, while processing a pap case.

FIG. 6 shows the "Add Mode" input and output. This provides the capability of adding comments, notes, supplemental reports, case clinical information, specimen clinical information, scratch pad entries, additional specimen comments, and additional diagnosis while processing a pap case.

FIG. 7 shows the "Read" command. This provides the capability of reading back comments, notes, supplemental reports, case clinical information, specimen clinical information, scratch pad, diagnosis, specimen comments and adequacy while processing a pap case.

FIG. 8 shows the "Remove" command. This provides the capability of removing individual comments, notes, supplemental reports, case clinical information, specimen clinical information while processing a pap case.

Figure 9:
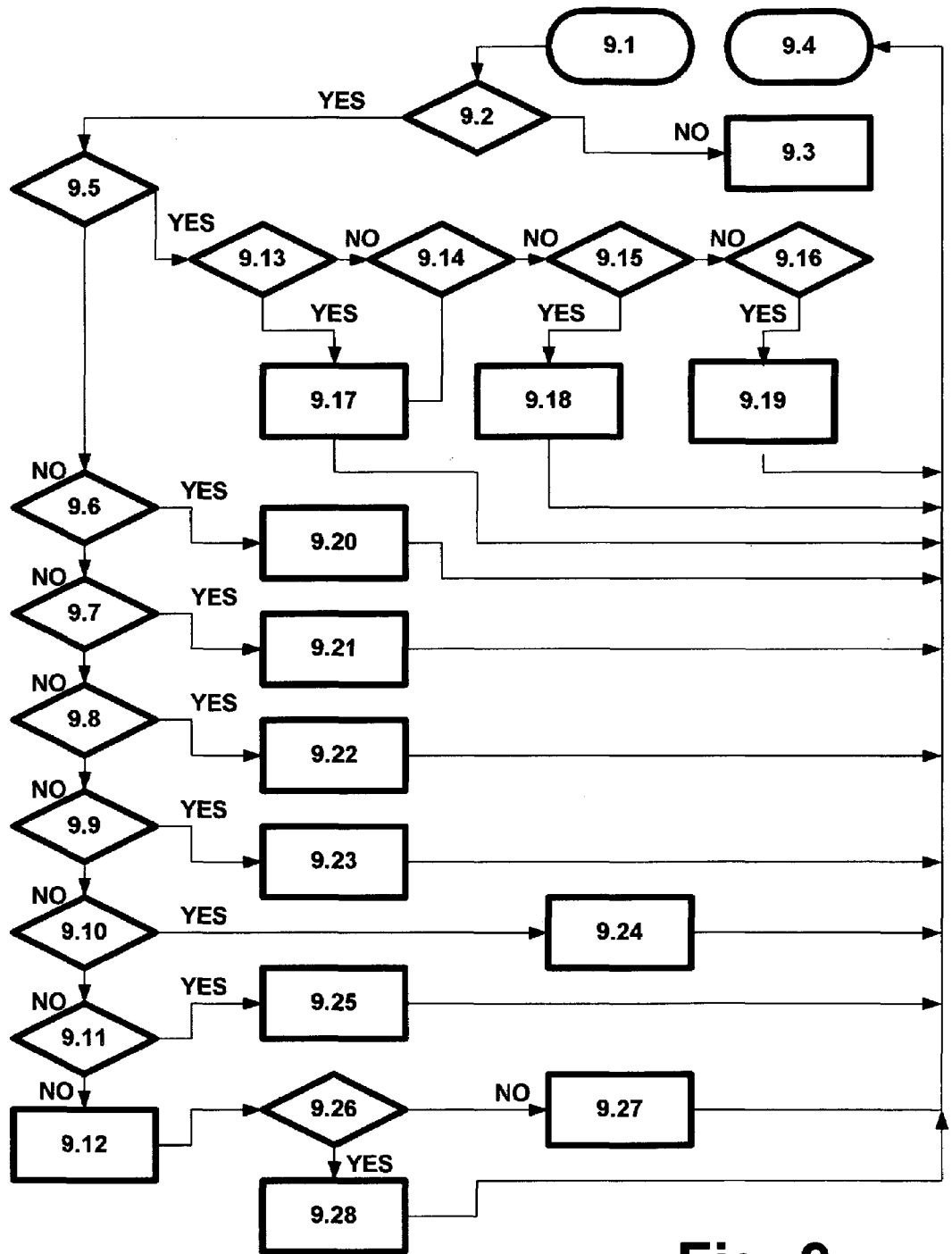
FIG. 9 is a flow diagram of the Common Vocabulary sub-system of the present invention.

The Common Vocabulary Sub-System—FIG. 9

FIG. 9 is a detailed block diagram of the common vocabulary sub-system shown generally in FIG. 2. The steps and components of this sub-system, as explained below, are numbered in correspondence with the numbered indicia in FIG. 9.

9.1 Application receives recognized user spoken input.
9.2 Is the spoken input one of the vocabulary phrases that are common to all vocabulary files?
9.3 See Flow Chart of Current Operation.
9.4 Application waits for spoken user input.
9.5 Is the spoken input recognized as a request to modify report information?
9.6 Is the spoken input "Clear the case"?
9.7 Is the spoken input "Back"?
9.8 Is the spoken input "Where am I"?
9.9 Is the spoken input "Sleep"?
9.10 Is the spoken input "Wake up"?
9.11 Is the spoken input "Repeat"?
9.12 The user input is "Log out".
9.13 Has the user requested addition to report information?
9.14 Has the user requested removal of report information?
9.15 Has the user requested removal of all report information?
9.16 Has the user requested hearing all report information?
9.17 Store the current operation. Set the type of report information to add or remove and set appropriate vocabulary file.
9.18 Remove all of the requested report information added during the current working of this case.
9.19 System reads all of the requested report information.
9.20 Clear the currently selected case. Set the current operation to Get Case and load the appropriate vocabulary file.
9.21 Remove the last entered information and reset the current operation to the last operation. Set the appropriate vocabulary file. Speak to the user the information that has been removed.
9.22 Speak to the user the current operation or report item being worked.
9.23 Speak to the user "Sleeping". Set appropriate vocabulary file and store the current operation as the last operation. This effectively sets the application to respond only to "Wake up".
9.24 Speak to the user "I'm awake." Set appropriate vocabulary file and set the current operation to the last operation.
9.25 Speak to the user the last item spoken by the application.
9.26 Is the current operation "Get Case"?

9.27 Speak to the user "You cannot log out in the middle of a case."

9.28 Set the appropriate vocabulary file. Speak to the user "Are you sure?".

Figure 10:
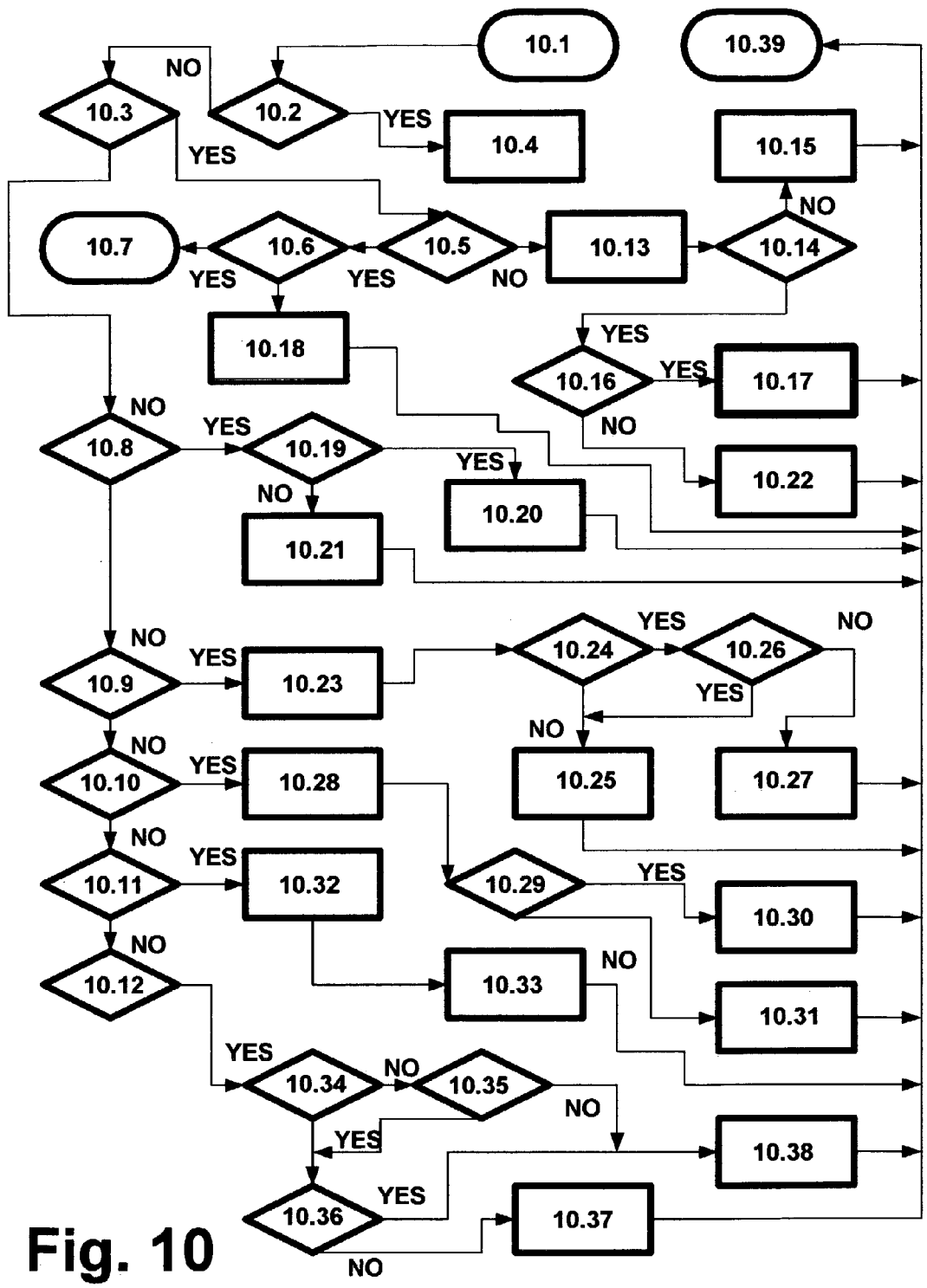
FIG. 10 is a flow diagram of the Current Operation sub-system of the present invention.

The Current Operation Sub-System—FIG. 10

FIG. 10 is a detailed block diagram of the current operation sub-system shown generally in FIG. 2. The steps and components of this sub-system, as explained below, are numbered in correspondence with the numbered indicia in FIG. 10.

10.1 Application receives recognized user spoken input.

10.2 Is the spoken input one of the vocabulary phrases that are common to all vocabulary files?

10.3 Is the Current Operation "Get Case"?

10.4 See Flow Chart of Common Vocabulary.

10.5 Did the user request to log out?

10.6 Is the input YES?

10.7 Log Out.

10.8 Is the Current Operation "Verify Case"?

10.9 Is the Current Operation "Review Adequacy"?

10.10 Is the Current Operation "Review Specimen"?

10.11 Is the Current Operation "Provide Diagnosis"?

10.12 Is the Current Operation "Sign Out Case"?

10.13 Convert spoken input into a case number. Search for case requested.

10.14 Was the case found?

10.15 Speak to user "No case found."

10.16 Has the case already been worked?

10.17 Speak to user "The found case has already been worked."

10.18 Remove request to log out.

10.19 Was the spoken input "Continue"?

10.20 Set this case as the selected case. Current Operation is set to Review Adequacy and the appropriate vocabulary file is set.

10.21 Speak to the user the requested information, which may be one of social, job, medical record number, or case number.

10.22 Speak to user the name of the patient on the found case. Set the Current Operation to Verify Case and load the appropriate vocabulary file.

10.23 Assign the specimens adequacy input by the user to the selected case. Speak to the user the specimen adequacy input for verification purposes.

10.24 Is the adequacy satisfactory?

10.25 Set the current operation to Review Specimen and load the appropriate vocabulary file.

10.26 Is the site Bethesda Compliant?

10.27 Set the current operation to Get Diagnosis and load the appropriate vocabulary file.

10.28 Assign the specimen's description by the user to the selected case. Speak to the user the specimen description input for verification purposes.

10.29 Is the adequacy satisfactory?

10.30 Set the Current Operation to Review Specimen and load the appropriate vocabulary file.

10.31 Set the current operation to Sign Out Case and load the appropriate vocabulary file.

10.32 Assign the diagnosis input by the user to the selected case. Speak to the user the diagnosis input for verification purposes.

10.33 Set the current operation to Sign Out Case and load the appropriate vocabulary file.

10.34 Did the user request a re-screen?

10.35 Did the user request a review?

10.36 Is the adequacy satisfactory?

10.37 Speak to the user "Unable to re-screen or review an inadequate specimen."

10.38 Determine if the case is selected for random re-screen. Perform database updates. Notify the user that the case has been signed out. Speak to the user the diagnosis and diagnosis category for verification purposes. Set the Current Operation to Get Case and load the appropriate vocabulary file.

10.39 Application waits for spoken user input.

OPERATION

In operation, a Get Case command matches the case number entered by the user with the case to be screened. If there is a match, the system speaks the name of the found matching case, sets the Current Operation to Verify Case, and loads the appropriate vocabulary file. If no match is found, the system says, "No match found." A Verify Case command causes the system to speak the requested information to the user for the selected case. If the case is verified, the system indicates that the user has verified the case and wishes to continue. The current operation then is set to Review Adequacy and the appropriate vocabulary file is loaded. In response to this command, the system stores the description of the specimen's adequacy for the selected case, sets the current operation to one of the following commands: Review Specimen Description, Provide Diagnosis, and Sign Out, and sets the appropriate vocabulary file. The Review Specimen Description command causes the system to store the description of the specimen for the selected case, sets the current operation to Provide Diagnosis or Sign Out, and sets the appropriate vocabulary file. The Provide Diagnosis command causes the system to store the diagnosis provided for the selected case, sets the current operation to Sign Out. The Sign Out command causes the system to update the database with the information provided by the user pertaining to the specimen's adequacy, description and diagnosis, and sets the Current Operation for Get Case.

What is claimed is:

1. A digital system for assisting the microscopic screening of cytology slides by a user, said system comprising:
    (a) a microphone adapted to receive voice input to be spoken by said user;
    (b) a speaker adapted to transmit voice output to be heard by said user;
    (c) a digital processor having an electronic database, a voice recognition unit, and a voice synthesizing unit;
    (d) said electronic database containing a plurality of patient cases in the form of electronic case representations identified by case numbers, a library of specimen comments related to cytology in the form of electronic specimen representations corresponding to digital text on deposit in said electronic database, and a library of diagnosis phrases related to cytology in the form of electronic diagnosis representations corresponding to digital text on deposit in said electronic database,
    (e) said voice recognition unit being operatively connected to said digital processor to convert speech received from said microphone to digital text on deposit in said electronic database;
    (f) said voice synthesizing unit being operatively connected to said digital processor to generate speech transmitted from said speaker to said user on the basis of said electronic specimen representations and said electronic diagnosis representations; and (g) a printer for combining a selected one of said case numbers with selected ones of said electronic specimen representations and said diagnosis representations to provide a cytology report.

2. A system for minimizing the effect of interruptions in and distractions from the attention needed by a user in screening a cytology slide by inducing the eye contact of said user with said cytology slide, said system comprising:

(a) a microphone for electronic recognition of selected voice input commands that are spoken by a user;

(b) a speaker for electronic generation of selected voice output alerts that are heard by said user;

(c) a computer for electronic processing of said voice inputs and said voice outputs for semi-automatic development of the elements of a cytology report; and a program for operating said computer, said program providing a Get Case procedure, a Verify Case procedure, a Review Adequacy procedure, a Review Specimen procedure, a Provide Diagnosis procedure, and a Sign Out procedure;

(d) said Get Case procedure attempting to match a case number entered by said user with the case in the to-be-worked list;

(e) said Verify Case procedure speaking requested information about said selected case to said user for said selected case;

(f) said Review Adequacy procedure presenting a description of said specimens' adequacy for said selected case and setting an appropriate vocabulary file;

(g) said Review Specimen procedure causing storage of a description of said specimen for said selected case, setting a current operation to Provide Diagnosis;

(h) said Provide Diagnosis procedure causing storage of a diagnosis provided for said selected case; and (i) said Sign Out procedure causing said system to update said database.

3. A system for inducing a cytologist to maintain eye contact with a cytology slide during scanning and marking by the use of interacting voice inputs from a user to said system via a microphone and voice outputs from said system to said user via a speaker, said system comprising:

(a) a voice input procedure which retrieves library phrases and voice shortcuts that describe pap case outcomes for creation and presentation of vocabulary files; and (b) a current operation procedure which retrieves current operations commands that are appropriate for selected vocabulary files;

(c) said voice inputs and said voice outputs being in the form of parsed phrases; (d) said voice inputs from said user and said voice outputs from said system enabling said user to speak input comments for conversion to text in an electronic scratch pad regarding visual observations being made during scanning, enabling said user to call up said input comments as voice outputs;

(e) said voice inputs from said user and said voice outputs from said system enabling said user to call up comments and diagnoses in the form of voice outputs from electronic comment and diagnosis vocabularies;

(f) said voice inputs from said user and said voice outputs from said system enabling said user to hear said voice outputs at any time; and (g) said voice inputs from said user and said voice outputs from said system enabling said user to assemble a selection of said voice outputs in the same text format for incorporation in a Cytology report.

4. A system for screening cytology slides by a user, said system comprising:

(a) a microscope having a focal frame and a stage moving a slide in X and Y directions in incrementally distinct scanning paths;

(b) a microphone adapted to receive voice input to be spoken by said user;

(c) a speaker adapted to transmit voice output to be heard by said user;

(d) a digital processor having an electronic database, a voice recognition unit, and a voice synthesizing unit;

(e) said electronic database containing a plurality of patient cases in the form of electronic case representations identified by case numbers, a library of specimen comments related to cytology in the form of electronic specimen representations corresponding to digital text on deposit in said electronic database, and a library of diagnosis phrases related to cytology in the form of electronic diagnosis representations corresponding to digital text on deposit in said electronic database;

(e) said voice recognition unit being operatively connected to said digital processor to convert speech received from said microphone to digital text on deposit in said electronic database;

(f) said voice synthesizing unit being operatively connected to said digital processor to generate speech transmitted from said speaker to said user on the basis of said electronic specimen representations and said electronic diagnosis representations; and (g) a printer for combining a selected one of said case numbers with selected ones of said electronic specimen representations and said diagnosis representations to provide a cytology report.

5. A process for screening cytology slides by a user, said process comprising:

(a) moving a cytology slide at the focal frame of a microscope in a series of incrementally distinct scanning paths;

(b) speaking into a microphone voice inputs of comment phrases and diagnosis phrases regarding said slide;

(c) electronically recognizing certain of said comment phrases and certain of said diagnosis phrases;

(d) electronically matching said certain of said comment phrases and said certain of said diagnosis phrases with corresponding selected comment phrases and corresponding selected diagnosis phrases, which have been electronically stored in a database;

(e) generating selected voice outputs corresponding to said selected comment phrases and said selected diagnosis phrases, and transmitting said voice outputs to be heard by said user; and (f) processing said selected comment phrases and said selected diagnosis phrases to provide a cytology report.

6. The process of claim 5 wherein said slide contains blood cells that have been stained and preserved.

7. The process of claim 6 wherein, substantially concurrently, certain of said cells are marked.

8. A process for inducing maintenance of eye contact with a cytology slide during scanning and marking by a user, said process comprising the steps of:

(a) transmitting voice inputs from a user to a digital processor via a microphone;

(b) receiving voice outputs from said digital processor a system via a speaker;

(c) electronically recognizing said voice inputs to provide electronic records thereof;

(d) electronically matching certain of said electronic records with certain of the electronic records of a library of electronic records;
(e) said electronic records of said library describing pap case outcomes;
(f) selected ones of said electronic records describing selected pap case outcomes; and
(g) assembling said selected ones of said electronic records to provide a medical report.

9. The process of claim 8 wherein said medical report contains a medical diagnosis.

10. The process of claim 8 wherein said voice inputs are in the form of parsed phrases.

11. The process of claim 8 wherein said voice outputs are in the form of parsed phrases.

12. The process of claim 8 wherein said voice inputs and said voice outputs are in the form of parsed phrases.

13. A system for inducing maintenance of eye contact with a cytology slide during scanning and marking by a user, said system comprising:
(a) means for transmitting voice inputs from a user to a digital processor via a microphone;
(b) means for receiving voice outputs from said digital processor a system via a speaker;
(c) means for electronically recognizing said voice inputs to provide electronic records thereof;
(d) means for electronically matching certain of said electronic records with certain of the electronic records of a library of electronic records;
(e) said electronic records of said library describing pap case outcomes;
(f) selected ones of said electronic records describing selected pap case outcomes; and
(g) means for assembling said selected ones of said electronic records to provide a medical report.

14. The system of claim 13 wherein said medical report contains a medical diagnosis.

15. The system of claim 13 wherein said voice inputs and said voice outputs are in the form of parsed phrases.

* * * * *